United States Patent [19]

Ohachi

[11] Patent Number: 4,612,340
[45] Date of Patent: Sep. 16, 1986

[54] MEDICAL DEVICE

[76] Inventor: Yoshinori Ohachi, 747, Kitamikata, Takatsu-ku, Kawasaki-shi, Kanagawa-ken, Japan

[21] Appl. No.: 585,859

[22] Filed: Mar. 2, 1984

[30] Foreign Application Priority Data

Mar. 9, 1983 [JP] Japan .................. 58-37283
Mar. 9, 1983 [JP] Japan .................. 58-37284

[51] Int. Cl.⁴ .................................. C08K 5/09
[52] U.S. Cl. ........................ 524/296; 523/300; 524/297; 524/432; 524/433; 604/408; 604/410
[58] Field of Search ............. 524/296, 297, 432, 433; 604/408, 410; 523/300

[56] References Cited

U.S. PATENT DOCUMENTS

| 2,325,951 | 8/1943 | Gresham | 524/296 |
| 2,956,976 | 10/1960 | Peciura | 524/433 |
| 3,395,111 | 7/1968 | Mazzolini et al. | 524/432 |
| 4,058,471 | 11/1977 | Glatti et al. | 524/432 |
| 4,464,502 | 8/1984 | Jacobs | 524/432 |

FOREIGN PATENT DOCUMENTS

| 648868 | 9/1962 | Canada | 524/433 |
| 56-41420 | 4/1981 | Japan | |
| 1028323 | 5/1966 | United Kingdom | |
| 1062311 | 3/1967 | United Kingdom | |
| 1163278 | 9/1969 | United Kingdom | |
| 1229521 | 4/1971 | United Kingdom | |
| 1229522 | 4/1971 | United Kingdom | |
| 1339265 | 11/1973 | United Kingdom | |
| 1487875 | 10/1977 | United Kingdom | |

OTHER PUBLICATIONS

Baum; Zinc Oxide: An Effective Weathering Stabilizer; "Elastomerics"; Mar. 1977; 524-432.
Patents Abstracts of Japan, vol. 5, No. 98 (C-60) (770), Jun. 25, 1981; and JP-A-56 41 240 (Sekisui Kagaku Kogyo K.K.) 17-04-1981 (Cat. D).
Chemical Abstracts, vol. 67, No. 20, p. 8617, No. 91307c.
Chemical Abstracts, vol. 97, No. 4, p. 39, No. 24743y.

Primary Examiner—Lewis T. Jacobs

[57] ABSTRACT

A radiation sterilized medical device made of a resin compound comprising 100 parts by weight of vinyl chloride resin, 0.001 to 5 parts by weight of at least one metal oxide selected from the group consisting of magnesium oxide, calcium oxide, and zinc oxide and 5 to 200 parts by weight of a dialkyl phthalate of the formula

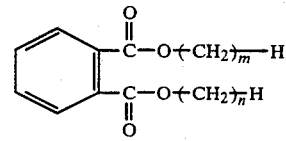

wherein m and n are each an integer of the value of substantially 6 to 12 and the average of m an n, $(m+n)/2$, is not more than 11.5. The invention also provides the method of preparing said medical device and the specified resin.

21 Claims, 3 Drawing Figures

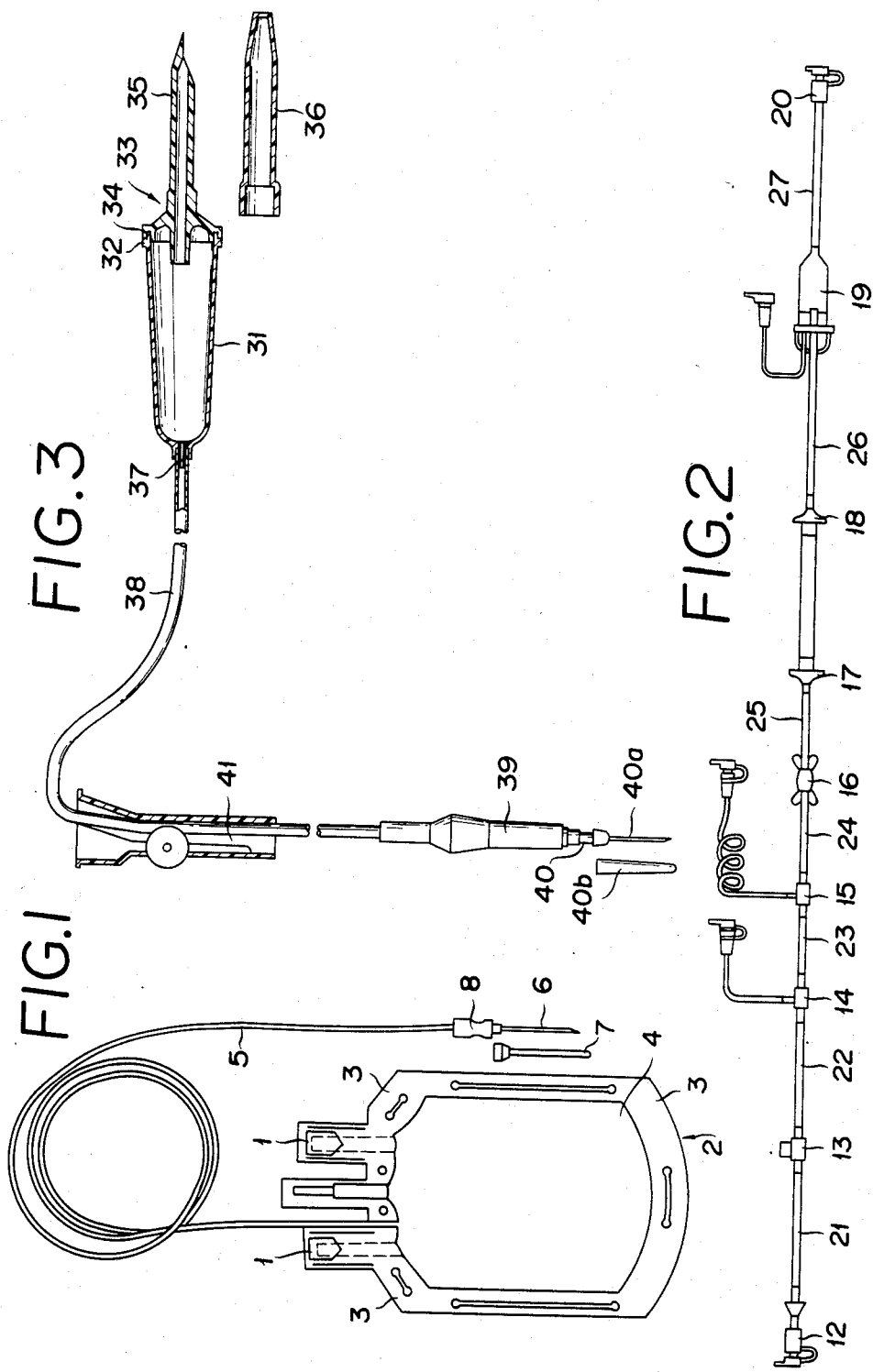

MEDICAL DEVICE

BACKGROUND OF THE INVENTION

1. Field of the Invention

This invention relates to a medical device, and particularly to a medical device capable of withstanding sterilization by radiation. More particularly, this invention relates to a medical device such as the tube for an administration set, which is made of vinyl chloride resin and, therefore, is capable of withstanding sterilization by radiation.

2. Description of Prior Arts

Heretofore, it has been customary for such medical devices as blood bag, solution administration set and catheter to be first sterilized as by the wet sterilization or the action of a sterilizing agent such as ethylene oxide gas and then stowed in respective packages similarly sterilized in advance or for them to be first contained in respective packages and thereafter subjected in situ to sterilization. In the case of the thermal sterilization, however, there has been entailed the problem that the synthetic resin used in such medical devices is required to offer heat resistance to the heat of sterilization and yield sparingly to thermal deformation. In the case of the sterilization with ethylene oxide gas, there has been involved the problem that, after the sterilization, a good deal of time is wasted before the sterilized medical devices will be free from ethylene oxide gas and then ready for use.

As a method for effecting required sterilization without requiring such use of heat or sterilizing agent, the method of sterilization by radiation has been recently proposed. Since this method is carried out at low temperatures, it no longer entails the requirement that the materials of medical devices should be capable of withstanding heat and shunning thermal deformation or the problem regarding the manner of handling such medical devices. The use of radiation nevertheless causes irradiated medical devices to suffer from adverse effects such as deterioration and discoloration. Particularly, medical devices made of or using flexible vinyl chloride resin, when sterilized by radiation entail the problem that they fail in the safety test which all medical devices are required to pass. For example, the vinyl chloride resin composition which has found popular acceptance for use in medical devices comprises 100 parts by weight of polyvinyl chloride, 30 to 80 parts by weight of di-2-ethylhexyl phthalate, about 0.01 to 5 parts by weight of a calcium-zinc type metallic soap as a stabilizer, about 0 to 10 parts by weight of epoxidized soybean oil as an assistant stabilizer, and optionally about 0 to 5 parts by weight of slidant. When a molded article of such flexible vinyl chloride resin was sterilized by exposure to radiation and thereafter tested by the "Standard for Blood Bag Set made of Vinyl Chloride Resin" (Ministry of Health and Welfare Standard), Notification No. SHOWA 40(1965)-448 of Ministry of Health and Welfare or the "Method for Testing Plastic Containers for Transfusion (Pharmacopieial Standard)" of the Tenth Amended General Testing Methods, No. 42, of the Japaneses Parmacopoeia to determine whether or not the molded article would discharge any extract and whether the extract, if any, would cause hemolysis, the results obtained by the irradiation at a dosage of 3 Mrads were found to exceed the tolerable limits. Thus, the resin proved to be rejectable as a material for medical devices destined to be sterilized by radiation. When the extract from the molded article was subjected to the cell toxicity test designed to ensure more reliable safety of containers, it was found to possess discernible toxicity.

A stabilizer such as zinc stearate, calcium stearate or magnesium stearate has hitherto been incorporated with the vinyl chloride resin. However, the amount of the stabilizer is larger. Such stabilizer also acts as a lubricant, so it bleeds out on the surface during the molding.

As the resin composition for medical use, a composition comprising 100 parts by weight of a vinyl chloride resin, 5 to 200 parts by weight of an ethylene-carbon monoxide-vinyl acetate copolymer and 0.001 to 10 parts by weight of powdered magnesium oxide or calcium oxide is known (Japanese Patent Open No. Sho 56(1981)-41240). The ethylene-carbon monoxide-vinyl acetate copolymer as a softening agent is apt to yield acetic acid during heat molding and the acetic acid is neutralized by magnesium oxide or calcium oxide. However, the above composition can be molded only below 120° C. If the composition is heated above 120° C., diacetic acid is enhanced. Further, if the medical device made of the composition is sterilized by radiation, acetic acid is apt to be produced. Thus if acetic acid is liberated, it will be extracted into medical solution or blood.

OBJECT OF THE INVENTION

An object of this invention, thereofre, is to provide an improved medical device.

Another object of this inveniton is to provide a medical device capable of withstanding sterilization by radiation.

Yet another object of this invention is to provide a medical device which, on exposure to radiation, sparingly discharge extract causing minimal hemolysis and showing no toxicity.

Still another object of this invention is to provide a vinyl resin composition for medical use.

SUMMARY OF THE INVENTION

The objects described above are attained by this invention providing a medical device which is made of a resin compound comprising 100 parts by weight of viny chloride resin, 0.001 to 5 parts by weight of at least one metal oxide selected from the group consisting of magnesium oxide, calcium oxide and zinc oxide, and 5 to 200 parts by weight of a plasticizer.

This invention is also a medical device wherein the content of the metal oxide falls in the range of 0.005 to 3 parts by weight based on 100 parts of the vinyl chloride resin content. This invention is also a medical device wherein the plasticizer contained therein is a dialkyl phthalate (the two alkyl groups each having substantially 6 to 13 carbon atoms). This invention is also a medical device wherein the dialkyl phthalate contained therein as the plasticizer is represented by the general formula I:

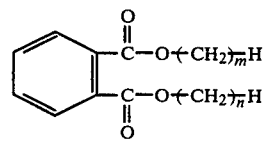

wherein m and n each stand for an integer of the value of substantially 6 to 12, providing that the average of the two integers, (m+n)/2, does not exceed 11.5. This invention is also a medical device wherein the integers represented by m and n in the general formula I and both substantially 7 to 12 and the average of the two integers, (m+n)/2, does not exceed 11 and, therefore, the phthalic dialkyl ester is particularly desired to be di-n-decyl phthalate or a mixture of n-decyl-(n-dodecyl) phthalate, di-n-decyl phthalate and di-n-dodecyl phthalate. This invention is also a medical device wherein the dialkyl phthalate content falls in the range of 10 to 100 parts by weight based on 100 parts by weight of the vinyl chloride resin content. This invention is also a medical device which is a container for preserving body fluid, particularly blood. This invention is also a medical device which is a catheter, a blood administration set, a solution administration set or a blood line.

The objects described above are also attained by this invention providing a vinyl resin composition medical use comprising 100 parts by weight of vinyl chloride resin, 0.001 to 5 parts by weight of at least one metal oxide selected form the group consisting of magnesium oxide, calcium oxide, and zinc oxide and 5 to 200 parts by weight of a plasticizer.

This invention is also a composition, wherein the amount of said metal oxide content in said resin composition falls in the range of 0.005 to 3 parts by weight based on 100 parts by weight of said vinyl chloride resin. This invention is also a composition, wherein said plasticizer is a dialkyl phthalate (wherein the two alkyl groups each have substantially 6 to 13 carbon atoms). This invention is a composition, wherein said dialkyl phthalate is represented by the general formula I.

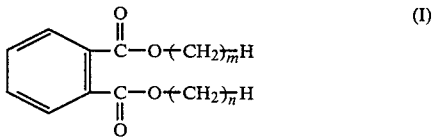

wherein m and n are each an integer of the value of substantially 6 to 12 and the average of m and n, (m+n)/2, is not more than 11.5. This invention is also a composition, wherein the amount of said dialkyl phthalate content in said resin compound is in the range of 10 to 100 parts by weight based on 100 parts by weight of said vinyl chloride resin content. This invention is also a composition, wherein m and n in said general formula I each stand for an integer of the value of substantially at least 7 and the average of m and n, (m+n)/2, is not more than 11. This invention is also a composition, wherein said dialkyl phthalate is selected from the group consisting of di-n-decyl phthalate and a mixture of n-decyl-(n-dodecyl)phthalate, di-n-decyl phthalate and di-n-dodecyl phthalate. This invention is also a composition, wherein said metal oxide is magnesium oxide.

BRIEF DESCRIPTION OF THE DRAWINGS

FIG. 1 is a front view illustrating a typical medical device as one embodiment of this invention, FIG. 2 is a schematic side view illustrating another medical device embodying this invention, and FIG. 3 is a cross section illustrating yet another medical device embodying this invention.

PREFERRED EMBODIMENTS OF THE INVENTION

The medical devices contemplated by the present invention are such medical device as bags and tubes for use in catheters, blood administration sets, solution administration sets, blood lines and blood bags; catheters themselves, and particularly tubes for solution administration sets; containers for packaging such medical devices as described above; and containers for packaging tablets and other forms of medicine.

Examples of the vinyl chloride resin contained in the resin composition to be used for the manufacture of the medical device of this invention include, besides the homopolymer of vinyl chloride, polyvinylidene chloride and copolymers between at least 40% by weight, more desirably at least 65% by weight, and most desirably at least 75% by weight, of vinyl chloride and monomer copolymerizable therewith. The average polymerization degree of the vinyl chloride resin is in the range of 400 to 3,000, more desirably 600 to 2,700, and most desirably 800 to 1,700. Examples of the comonomer to be copolymerized with vinyl chloride include vinylidene chloride, ethylene, propylene, vinyl acetate, vinyl bromide, vinyl fluoride, styrene, vinyl toluene, vinyl pyridine, acrylic acid, alkyl acrylates (such as, for example, methyl acrylate, ethyl acrylate, isopropyl acrylate, n-butyl acrylate and 2-ethylhexyl acrylate), methacrylic acid, alkyl methacrylates (such as, for example, methyl methacrylate, ethyl methacrylate and 2-ethylhexyl methacrylate), acrylonitrile, and methacrylonitrile. Optionally, the vinyl chloride resin may be used in combination with styreneacrylonitrile copolymer or styrenemethacrylonitrile copolymer.

The most prominent characteristic of the present invention is the fact that the vinyl chloride resin is used in the resin compound in combination with at least one metal oxide selected from the group consisting of magnisium oxide, calcium oxide and zinc oxide. Of the three metal oxides, magnesium oxide is the most desirable choice. The amount of the metal oxide to be contained in the resin composition is in the range of 0.001 to 5 parts by weight, preferably 0.005 to 3 parts by weight, based on 100 parts by weight of the vinyl chloride resin content. If the metal oxide content is less than 0.001 part by weight, the improvement in the results of the extraction test aimed at by the addition of this metal oxide is not attained. If this content exceeds 5 parts by weight, the increment of the effect is no longer obtained.

As the plasticizer for use in the resin composition of this invention, any of the plasticizers which are generally suitable for use with vinyl chloride resin can be adopted. This plasticizer, however, is desired to be a dialkyl phthalate represented by the general formula II:

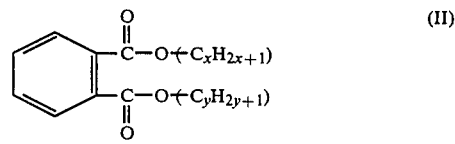

In the general formula, x and y each stand for an integer of the value of at least 6 and the average of x and y, (x+y)/2, is not more than 13, and more desirably x and y each stand for an integer of the value of substantially 7 to 13 and the average of x and y, (x+y)/2, is not more than 12. If either or both of x and y are not more than 4, the diester has the possibility of manifesting toxicity. If x and y are both 5, the diester is not commercially available and is hard to obtain. If the average, (x+y)/2, exceeds 13, the diester exhibits poor miscibility with the vinyl chloride resin and, therefore, is substantially infeasible as a pasticizer. Besides, x and y need not be one kind of alchol. The ester may issue from a mixture of two alchols of different chain lengths.

It is imperative that the vinyl chloride resin composition containing the plasticizer described above should incorporate the aforementioned metal oxide. If the metal oxide content in the resin composition is less than 0.001 part by weight, the resin composition no longer passes the standard test of Ministry of Health and Welfare and does not suit use in the production of the medical device contemplated by the present invention.

The dialkyl phthalates described above include phthalic diesters of linear fatty alcohols represented by the general formula I:

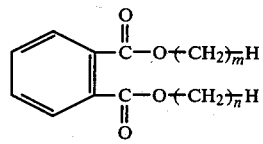

In the general formula, m and n each stand for an integer of the value of substantially 6 to 12 and the average of m and n, (m+n)/2, is not more than 11.5, and more desirably m and n each stand for an integer of the value of substantially 7 to 12 and the average of m and n, (m+n)/2, is not more than 11. If either or both of m and n are not more than 4, the phthalic diester has the possibility of manifesting toxicity. If m and n are both 5, the phthalic diester is not commercially available and, therefore, is hard to obtain. If the average of m and n, (m+n)/2, exceeds 11.5, the phthalic diester manifests poor miscibility with the vinyl chloride resin and is substantially infeasible as a plasticizer. Besides, m and n need not be such as to give rise to independent alcohols. The ester may issue from a mixture of two alcohols of different chain lengths. If the alcohols as components of the phthalic diester are alcohols of straight chains, the resin compound during sterilization by radiation discharges extract along the tolerable level fixed by the Japanese Pharmacopoeia and this extract does not produce cell toxicity at all. For the resin compound to be advantageously used in the production of the medical device, therefore, these alcohols are desired to be alcohols of linear chains.

Examples of the dialkyl phthalate of the aforementioned general formula I are esters of phthalic anhydride with sole alcohols or mixed alcohols and include, for example, di-n-hexyl phthalate, di-n-heptyl phthalate, di-n-octyl phthalate, di-n-nonyl phthalate, di-n-decyl phthalate, di-n-undecyl phthalate, di-n-dodecyl phthalate, n-hexyl-(n-heptyl)phthalate, n-hexyl-(n-octyl)phthalate, n-hexyl-(n-nonyl)phthalate, n-hexyl-(n-decyl)phthalate, n-hexyl-(n-undecyl)phthalate, n-hexyl-(n-dodecyl)phthalate, n-heptyl-(n-octyl)phthalate, n-heptyl-(n-nonyl)phthalate, n-heptyl-(n-decyl)phthalate, n-heptyl-(n-undecyl)phthalate, n-heptyl-(n-dodecyl)phthalate, n-octyl-(n-nonyl)-phthalate, n-octyl-(n-decyl)-phatalate, n-octyl-(n-undecyl)phthalate, n-octyl-(n-dodecyl)phthalate, n-nonyl-(n-decyl)phthalate, n-nonyl-(n-undecyl)phthalate, n-nonyl-(n-doecyl)phthalate, n-decyl-(n-undecyl)phthalate, n-decyl-(n-dodecyl)phthalate, n-octyl-(n-decyl)(dodecyl)phthalate and mixtures thereof. In all these dialkyl phthalates, the most desirable choices are di-ndecyl phthalate and a mixture of n-decyl-(n-dodecyl)phthalate, di-n-decyl phthalate and di-n-dodecyl phthalate.

The amount of the plasticizer content in the resin composition falls in the range of 5 to 200 parts by weight, more desirably 8 to 120 parts by weight, and most desirably 10 to 100 parts by weight, based on 100 parts by weight of the vinyl chloride resin content. Particularly, the plasticizer represented by the aforementioned general formula II manifests an advantageous effect. The plasticizer represented by the aforementioned general formula I manifests an outstanding effect.

When required, the vinyl chloride resin compound may further incorporate therein a metallic soap between calcium or zinc on one hand and stearic acid, lauric acid, ricinoleic acid, or naphthenic acid on the other hand, an epoxidized vegetable oil such as epoxidized soybean oil or epoxidized linseed oil, a slidant, or an antioxidant. The aforementioned plasticizer may be used, as conventionally known, in the form of a high molecular compound. For example, polychloroprene resin or thermoplastic polyurethane resin may be used by the technique of polymer blend.

Now, the medical device of this invention will be described below by citing a blood bag as one embodiment of the invention, with reference to the accompanying drawings. FIG. 1 illustrates a blood bag. A blood bag 2 made of vinyl chloride resin composition and provided with a plurality of outlets 1 each fitted with a peel tab has the peripheral edge thereof sealed as by high-frequency heading or some other heating means. A tube 5 made of vinyl chloride resin compound is connected to the blood bag so as to communicate with an inner space 4 of the blood bag. The tube 5 is provided at the leading end thereof with a needle base 8. To this needle base 8 is fastened a piercing needle 6. This piercing needle 7 is adapted to be sheathed with a cap 7.

FIG. 2 illustrates a typical arterial blood line as another embodiment of this invention. As is noted from the diagram, this blood line comprises a shunt adapter 12 provided with a priming cap 11, self-sealing injection port 13, T-shaped tubes 14, 15, a negative pressure pillow 16, pump-segment connectors 17, 18, a drip chamber 19, and a port connector 20, and tubes 21, 22, 23, 24, 25, 26 and 27 made of the aforementioned vinyl chloride resin compound and adapted to interconnect the components described above.

FIG. 3 is a solution administration set as another embodiment of this invention. In this set, an instillator is formed by placing a flange member 34 formed near the tip of an opening of a rigid cap member 33 produced by injection molding polypropylene, for example, fast in contact with a flange member 32 formed near the tip of an opening of a flexible, transparent tubular member 31 produced by injection molding a propylene-α-olefin copolymer and joining these two flange members by ultrasonic fusion by causing an oxcillator of an ultrasonic welder (not shown) to act upon the flange member 34 side. The cap member has a vial needle 35 integrally formed therewith. When necessary, the vial needle 35 is sheathed with a protective cap 36. At one end of the aforementioned flexible, transparent tubular member 31, there is formed a port 37. To this port 37 is connected a flexible tube 38 made of the aforementioned vinyl chloride resin compound and adapted to transfer a medical liquid. When necessary, a flexible connector 39 made of rubber and a connector 40 made of a rigid material are connected to the tip of the flexible tube 38. To the leading end of the connector 40 is connected, when necessary, a piercing needle 40a adapted to be plunged into the vein. Optionally, the piercing needle 40a is sheathed with a protective cap 40b. In the intervening portion, a pinch 41 is fitted so as to clamp the aforementioned flexible tube 38.

The medical device of this present invention has been described by citing a blood bag, a blood line, and a solution administration set each as emboyding the present invention. This invention can further be embodied as a container for preserving blood, a blood administration system, a solution administration system, a catheter, and a tube for dialysis in much the same way as described above. Since the aforementioned molded article made of vinyl chloride resin excels in ability to withstand sterization by radiation, tubes, catheters, and particularly tubes for solution administration sets show highly satisfactory results when they are made of this resin compound.

The medical devices contemplated by the present invention prove particularly advantageous when they are sterilized by radiation.

Examples of the radiation which is advantageously used for the sterilization of the medical device of this invention are elctromagnetic radiations such as gamma ray and elctron beam. The intensity of this radiation is in the range of 1 to 5 Mrads, preferably 1.5 to 3 Mrads.

Now, the present invention will be described more specifically below with reference to working examples.

EXAMPLE 1 AND CONTROL 1

With rolls having the surface temperature kept at 160° C., 100 parts by weight of polyvinyl chloride of an average polymerization degree of about 1,250, 50 parts by weight of a phthalic diester of a branched configuration satisfying the general formula II by having substntially 8 as the value of each of x and y (di-2-ethylhexyl phthalate) (DOP: made by Kyowa Hakko Kogyo Co., Ltd.), 0.5 part by weight of magnesium oxide (MgO), and suitable amounts of a stabilizer and a slidant of the grade generally accepted for use in the medical grade vinyl chloride resin compound were blended and the resultant blend was molded to produce a pressed sheet about 0.4 mm in thickness (Example 1).

By following the precedure described above, except that addition of magnesium oxide was omitted, there was similarly produced a pressed sheet (Control 1).

These pressed sheets were irradiated with 3 Mrads of gamma ray and were then tested by the "Standard for Blood Bag Set made of Vinyl Chloride Resin (Ministry of health and Welfare Standard), Notification No. SHOWA 40(1965)-448 of Ministry of health and Welfare. The results were as shown in Table 1.

From the above result, in Example 1, vinyl chloride resin compound for medical use having excellent radiation sterilization resistance which can pass the above Standard which is the most sever standard for the medical device enacted by Pharmaceutical Affairs Law and can be used as catheter, solution administration set, blood line and blood bag was obtained.

TABLE 1

| Item of test | Toleration | Control | Example 1 |
|---|---|---|---|
| Appearance | Colorless and | Colorless and | Colorless and |

TABLE 1-continued

| Item of test | Toleration | Control | Example 1 |
|---|---|---|---|
| | transparent | transparent | transparent |
| Change in pH | 2.0 max | 2.41 | 0.64 |
| 0.01 NKMnO$_4$ consumed | 2.0 ml max. | 1.57 | 0.77 |
| Chloride | 1.1 ml max. | 1.1 ml max. | 1.1 ml max. |
| Sulfate | 1.0 ml max. | 1.0 ml max. | 1.0 ml max. |
| Ammonium | 1.0 ml max. | 1.0 ml max. | 1.0 ml max. |
| Residue on evaporation | 5 mg max. | 0.4 mg | 0.4 mg |

EXAMPLE 2 AND CONTROL 2

With rolls having the surface temperature kept at 160° C., 100 parts by weight of polyvinyl chloride of an average polymerization degree of about 1,250, 50 parts by weight of a phthalic diester satisfying the general formula I by having stustantially 10 as the value of each of m and n (di-n-decyl phthalate) (Vinysize #105 made by Kao Soap Co., Ltd.), 0.5 parts by weight of magnesium oxide (MgO), and suitable amounts of a stabilizer and a slidant generally accepted for use with the medical grade vinyl chloride resin compound were blended and the resultant blend was molded to ptoduce a pressed wheet about 0.4 mm in thickness (Example 2). By following the procedure described above, except that addition of magnesium oxide was omitted, there was similarly obtained a pressed sheet (Control 2).

These pressed sheets and the pressed sheet of Control 1 were irradiated with 3 Mrads of gamma ray and then tested by the "Method for Testing Plastic Containers for Transfusion (Pharmacopoeial Standard)" of the Tenth Amended General Testing Methods, No. 42, of the Japanese Pharmacopeia. The results were as shown in Table 2. Further, cell toxicity test was carried out to obtain the results of Table 3. From these results, phthalic diesters esterified with an alcohol having straight chain can provide a medical vinyl chloride resin compound which can satisfy the Pharmacopeia standard, does not show cell toxicity, has high safety and can be sterilized by irradiation. Further, it can pass the Pharmacopeia standard which is required the safety of the highest level as testing method for medical vinyl chloride resin and also can pass the cell toxicity test which has the highest sensitivity as screening test for toxicity, so it is the medical vinyl chloxide resin compound which can be used in whole use without limiting their use and can be sterilized by radiation. The cell toxicity test was carried out as follows.

Method for cell toxicity test:

The cell toxicity test was carried out in accordance with the Toplin Method (Toplin, I: Cancer Ros. 19, 959 (1959) "Method for Toxicity Test, Explanation, Evaluation, and Problems, pp 171–172, 186–189).

The usefulness of this cell toxicity test is described in 82/1 Polymer Feasibility Lictures, collection of Summaries of Lectures, "Method for Testing Plastic Materials and Problems Encountered" pp 74–76." Although this method had not yet been officially adopted, it is useful in ascertaining safety of a given material.

Specifically, this test was conducted by placing 1 g of sliced test pieces in 3 ml of culture medium, keeping the medium at 121° C. for 20 minutes to induce possible extraction, diluting the resultant extraction medium with a reference medium, and administering the diluted medium to subject cell. The cell used in this test was HeLa.

TABLE 2

| Test item | Tolerance | Control 1* | Example 2*** | Control 2** |
|---|---|---|---|---|
| Appearance | Colorless and transparent | Colorless and transparent | Colorless and transparent | Colorless and transparent |
| Change in pH | 1.5 max. | 2.48 | 0.71 | 2.30 |
| 0.01N KMnO$_4$ consumed (ml) | 1.0 max. | 1.71 | 0.66 | 0.92 |
| Foaming | Extinction of foam within 3 minutes | Foam vanished within 3 minutes | Foam vanished within 3 minutes | Foam vanished within 3 minutes |
| Chloride (ml) | 0.7 max. | 0.7 max. | 0.7 max. | 0.7 max. |
| Sulfate (ml) | 2.0 max. | 2.0 max. | 2.0 max. | 2.0 max. |
| Ammonium (ml) | 0.5 max. | 0.5 max. | 0.5 max. | 0.5 max. |
| Phosphate (ml) | 0.3 max. | 0.3 max. | 0.3 max. | 0.3 max. |
| Distillation residue (ml) | 1 max. | 0.5 | 0.4 | 0.4 |
| Ultraviolet absorption | | | | |
| 230–241 mm | 0.08 max. | 0.19 | 0.05 | 0.06 |
| 241–350 mm | 0.05 max. | 0.10 | 0.02 | 0.02 |
| Hemolysis | No hemolysis detected | Hemolysis occured | No hemolysis detected | Hemolysis occured |

*Di-2-ethylhexyl phthalate incorporated as plasticizer and addition of MgO omitted.
**Di-n-decyl phthalate incorporated as plasticizer.
***Di-n-decyl phthalate incorporated as plasticizer and addition of MgO omitted.

TABLE 3

| Concentration of extracted medium | Control 1 | Example 2 | Control 2 |
|---|---|---|---|
| 100% (no dilution involved) | 2 | 0 | 0 |
| 67% | 0 | 0 | 0 |
| 33% | 0 | 0 | 0 |

Scale for rating toxicity:

0: Absence of cell toxicity (absolutely no difference from blank recognized).
1: Increase of dead cells (conspicuous signs of malformation and poor propagation, while the number of surviving cells was large).
2: Death of nearly all cells or all the cells verging on death.
3: Complete extinction of all the cells.

EXAMPLE 3–5

Medical grade vinyl chloride resin compounds were prepared by following the procedure of Example 1 except that the kind and amount of plasticizer and the kind and amount of metal oxide as a stabilizer were varied as indicated in Table 4. In the three resin compounds thus produced, only that of Example 5 was white and translucent.

A sheet for a blood bag was produced by using the composition of Example 3, a tube 5 by the composition of Example 4, and a needle base 8 by the composition of Example 5 respectively, to complete blood bag illustrated in the drawing. This blood bag was sterilized by exposure to 3 Mrads of gamma ray. Then, they were subjected to the same test as indicated in Example 2. The results were as shown in Tables 5–6.

TABLE 4

| | Example 3 | Example 4 | Example 5 |
|---|---|---|---|
| Plasticizer (kind) | Di-n-decyl phthalate | Phthalic diester mixture obtained by n-decyl alcohol and n-dodecyl alcohol | Phthalic diester mixture obtained by n-decyl alcohol and n-dodecyl alcohol |
| (amount) | 60 | 70 | 15 |
| Stabilizer (kind) | Magnesium oxide | Calcium oxide | Zinc oxide |
| (amount) | 0.1 | 0.3 | 0.05 |

TABLE 5

| Test item | Example 3 | Example 4 | Example 5 |
|---|---|---|---|
| Appearance | Colorless and transparent | Colorless and transparent | Colorless and transparent |
| Change of pH | 0.80 | 0.92 | 0.57 |
| KMnO$_4$ consumed (ml) | 0.58 | 0.70 | 0.41 |
| Foaming | Foam vanished within 3 minutes | Foam vanished within 3 minutes | Foam vanished within 3 minutes |
| Chloride (ml) | 0.7 max. | 0.7 max. | 0.7 max. |
| Sulfate (ml) | 2.0 max. | 2.0 max. | 2.0 max. |
| Ammonium (ml) | 0.5 max. | 0.5 max. | 0.5 max. |
| Phosphate (ml) | 0.3 max. | 0.3 max. | 0.3 max. |
| Distillation residue (ml) | 0.2 | 0.4 | 0.2 |
| Ultraviolet absorption | | | |
| 230–241 mm | 0.06 | 0.05 | 0.05 |
| 241–350 mm | 0.02 | 0.02 | 0.02 |
| Hemolysis | No hemolysis detected | No hemolysis detected | No hemolysis detected |

TABLE 6

| Concentration of extracted medium | Example 3 | Example 4 | Example 5 |
|---|---|---|---|
| 100% (no dilution involved) | 0 | 0 | 0 |
| 67% | 0 | 0 | 0 |
| 33% | 0 | 0 | 0 |

As described above, the medical device contemplated by the present invention is made of a resin compound comprising 100 parts by weight of vinyl chloride resin, 0.001 to 5 parts by weight of at least one metal oxide selected from the group consisting of magnetisum oxide, calcium oxide and zinc oxide, and 5 to 200 parts by weight of a plasticizer. Thus, the medical device molded by using this resin compound is suitable for sterilization by radiation. When a dialkyl phthalate represented by the general formula II is used as a plasticizer, then the resin composition exhibits excellent properties in the standard tests specified by the Ministry of health and Welfare. When a di-n-alkyl phthalate represented by the general formula I is used as a plasticizer, the resin composition exhibits excellent properties in the tests specified by the Japanese Pharmacopoeia and also shows quite satisfactory results in the cell toxicity test.

These advantageous effects are particularly conspicuous when the amount of the metal oxide content in the resin compound falls in the range of 0.005 to 3 parts by weight based on 100 parts by weight of the vinyl chloride resin content. When the amount of the plasticizer to be incorporated in the resin composition is selected in the range of 10 to 100 parts by weight based on 100 parts by weight of the vinyl chloride resin content, then the medical devices made of the resin comosition exhibit outstanding mechanical strength and flexibility. When this resin compound is used in the production of body fluid containers such as containers for the preservation of blood and medical devices such as catheters, blood administration sets, solution administration sets and blood lines and particularly such medical devices as tubes for solution administration sets, and so onwhich are exposed to direct contact with body fluids or solution for administration, the produced medical devices have no possibility of discharging extracts or causing hemolysis or manifesting toxicity. Thus, they prove highly useful.

As a standard on safety of medical synthetic resin, ther is the "Standard for Blood Bag Set made of Vinyl Chloride Resin" Ministry of Health and Welfare Standard of Japan, Notification No. SHOWA 40(1965)-448 which is the most sever standard in addition to the standard about blood administration set, solution administration set, blood bag, etc. notified by Ministry of Health and Welfare enacted based on Pharmaceutical Affairs Law, such as "Standard for Disposable Solution and Blood Administration Sets" (Notification No. SHOWA 45(1970)-301 of Ministry of Health and Welfare of Japan) and "Standard for Disposable Blood Collecting Instrument" (Notification No. SHOWA 45(1970)-300 of Ministry of Health and Welfare of Japan), and the medical vinyl chloride resin compound incorporated with the metal oxide can provide a medical material having excellent radiation sterilization resistance which can satisfy the standard even after sterilized by radiation. As the plasticizer for the medical vinyl chloride compound, dialkyl phthalate such as di-2-ethylhexyl phthalate is preferable.

On the other hand, specially high safety is required in a plastic container for solution administration which is expected to be sterilized by high pressure steam, it is necessary to pass the standard described in "Method for Testing Plastic Containers for Transfustion" of the Tenth Amended General Testing Methods, No. 42, of Japanese Pharmacopeia, and higher safety than other standards for medical container made of plastic is required considering extraction, hemolysis, etc. On the contrary, the device of the present invention can pass all of these standards.

What is claimed is:

1. A radiation sterilized medical device made of a resin compound comprising 100 parts by weight of vinyl chloride resin, 0.001 to 5 parts by weight of at least one metal oxide selected from the group consisting of magnesium oxide, calcium oxide, and zinc oxide and 5 to 200 parts by weight of a dialkyl phthalate of the formula

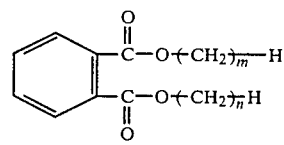

wherein m and n are each an integer of the value of substantially 6 to 12 and the average of m and n, $(m+n)/2$, is not more than 11.5.

2. The medical device of claim 1, wherein said dialkyl phthalate is in an amount from 10 to 100 parts by weight.

3. The medical device of claim 1, wherein m and n each stand for an integer of the value of substantially at least 7 and the average of m and n, $(m"n)/2$, is not more than 11.

4. The medical device of claim 3, wherein said dialkyl phthalate is selected from the group consisting of di-n-decyl phthalate and a mixture of n-decyl-(n-dodecyl)phthalate, di-n-decyl phthalate and di-n-dodecyl phthalate.

5. The medical device of claim 1, wherein said metal oxide is magnesium oxide.

6. The medical device of claim 1, wherein said sterilization by radiation is sterilization by gamma radiation.

7. The medical device of claim 1, wherein said medical device is a tube.

8. The medical device of claim 7, wherein said tube is a tube for a solution administration set.

9. The medical device of claim 1, wherein said dialkyl phthalate is in an amount from 10 to 100 parts by weight; said dialkyl phthalate is selected from the group consisting of di-n-decyl phthalate and a mixture of n-decyl-(n-dodecyl)phthalate, di-n-decyl phthalate and di-n-dodecyl phthalate; said metal oxide is magnesium oxide and the radiation used to sterilize said medical device is gamma ray radiation.

10. The medical device of claim 9, which is used to store blood or transport blood or both store and transport blood.

11. The medical device of claim 1, which is used to store blood or transport blood or both store and transport blood.

12. A process for preparing a radiation sterilized medical device which comprises molding a resin compound to form a medical device comprising 100 parts by weight of vinyl chloride resin, 0.001 to 5 parts by weight of at least one metal oxide selected from the group consisting of magnesium oxide, calcium oxide, and zinc oxide and 5 to 200 parts by weight of a dialkyl phthalate of the formula

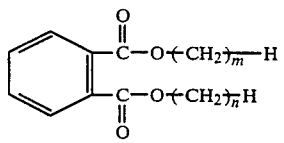

wherein m and n are each an integer of the value of substantially 6 to 12 and the average of m and n, $(m+n)/2$, is not more than 11.5; and sterilizing said molded device by radiation.

13. The process of claim 12, wherein said dialkyl phthalate is in an amount from 10 to 100 parts by weight.

14. The process of claim 12, wherein m and n each stand for an integer of the value of substantially at least 7 and the average of m and n, (m+n)/2, is not more than 11.

15. The process of claim 14, wherein said dialkyl phthalate is selected from the group consisting of di-n-decyl phthalate and a mixture of n-decyl-(n-dodecyl)phthalate, di-n-decyl phthalate and di-n-dodecyl phthalate.

16. The process of claim 12, wherein said metal oxide is magnesium oxide.

17. The process of claim 12, wherein said sterilization by radiation is sterilization by gamma ray radiation.

18. The process of claim 12, wherein said medical device is a tube for a solution administration set.

19. The process of claim 12, wherein said medical device is used to store or transport blood or to both store and transport blood.

20. The process of claim 19, wherein said dialkyl phthalate is in an amount from 10 to 100 parts by weight; said dialkyl phthalate is selected from the group consisting of di-n-decyl phthalate and a mixture of n-decyl-(n-dodecyl)phthalate, di-n-decyl phthalate and di-n-dodecyl phthalate; said metal oxide is magnesium oxide and the radiation used to sterilize said medical device is gamma ray radiation.

21. The process of claim 18, wherein said dialkyl phthalate is in an amount from 10 to 100 parts by weight; said dialkyl phthalate is selected from the group consisting of di-n-decyl phthalate and a mixtue of n-decyl-(n-dodecyl)phthalate, di-n-decyl phthalate and di-n-dodecyl phthalate; said metal oxide is magnesium oxide and the radiation used to sterilize said medical device is gamma ray radiation.

* * * * *

UNITED STATES PATENT AND TRADEMARK OFFICE
CERTIFICATE OF CORRECTION

PATENT NO. : 4,612,340
DATED : September 16, 1986
INVENTOR(S) : OHACHI It is certified that error appears in the above-identified patent and that said Letters Patent is hereby corrected as shown below:

Title page, left column, under Section "[76] Inventor", insert the following:

--[73] Assignee: Terumo Kabushiki Kaisha--.

Column 8, line 25, change "ptoduce" to --produce--.

Column 8, line 26, change "wheet" to --sheet--.

Column 12, line 27 (Claim 6), after "gamma" insert --ray--.

Signed and Sealed this

Sixth Day of April, 1993

Attest:

STEPHEN G. KUNIN

*Attesting Officer*   Acting Commissioner of Patents and Trademarks